US006408201B1

(12) United States Patent
Foo et al.

(10) Patent No.: US 6,408,201 B1
(45) Date of Patent: Jun. 18, 2002

(54) METHOD AND APPARATUS FOR EFFICIENT STENOSIS IDENTIFICATION IN PERIPHERAL ARTERIAL VASCULATURE USING MR IMAGING

(75) Inventors: Thomas K. F. Foo, Rockville; Vincent B. Ho, North Bethesda, both of MD (US)

(73) Assignees: General Electric Company, Milwaukee, WI (US); Uniformed Services University of Health Sciences, Bethesda, MD (US); Department of Defense, United States Government, Washington, DC (US)

( * ) Notice: Subject to any disclaimer, the term of this patent is extended or adjusted under 35 U.S.C. 154(b) by 55 days.

(21) Appl. No.: 09/591,300

(22) Filed: Jun. 9, 2000

(51) Int. Cl.[7] .................................................. A61B 5/05
(52) U.S. Cl. ..................... 600/410; 600/419; 600/420; 382/128; 324/300; 324/307
(58) Field of Search ................................. 600/420, 407, 600/419, 410; 382/128; 324/300, 307

(56) References Cited

U.S. PATENT DOCUMENTS 5,872,861 A * 2/1999 Makram-Ebeid ............ 382/130
6,240,311 B1 * 5/2001 Prince ......................... 600/420
6,259,940 B1 * 7/2001 Bernstein et al. ........... 600/410

OTHER PUBLICATIONS

Moran PR. A flow velocity zeugmatographic interlace for NMR imaging in humans. *Magnetic Resonance Imaging* 1982; 1: 197–203.
Bryant DJ, Payne JA, Firmin DN, and Longmore DB. Measurement of flow with NMR imaging using a gradient pulse and phase difference technique. *J. Comput Assist Tomogr* 1984; 8: 588–93.

van Dijk P. Direct cardiac NMR imaging of heart wall and blood flow velocity. *J. Comput Assist Tomogr* 1984; 8: 429–36.
Nayler GL, Firmin DN, and Longmore DB. Blood flow imaging by cine magnetic resonance. *J. Comput Assist Tomogr* 1986; 10: 715–22.
Swan JS, Grist TM, Weber DM, Sproat IA, and Wojtowycz MM. MR angiography of the pelvis with variable velocity encoding and a phase–array coil. *Radiology* 1994; 190:363–9.
Swan JS, Weber DM, Grist TM, Wojtowycz MM, Korosec FR, and Mistretta CA. Peripheral MR angiography with variable velocity encoding. Work in progress. *Radiology* 1992; 184: 813–7.
Ehman RL, Felmlee JP. Adaptive technique for high definition MR imaging of moving structures. *Radiology* 1998; 173: 255–263.

(List continued on next page.)

Primary Examiner—Marvin M. Lateef
Assistant Examiner—Jeoyuh Lin
(74) Attorney, Agent, or Firm—Timothy J. Ziolkowski, Esq.; Carl B. Horton, Esq.; Michael A. Della Penna, Esq.

(57) ABSTRACT

A method and apparatus is disclosed to initially screen a patient's peripheral arterial vasculature for lesions, or stenotic vessels, using MR technology, and then grading the severity of any located stenosis. The invention includes tracking the passage of a contrast agent bolus through a patient, while acquiring a series of first MR images having low resolution. This initial examination uses flow sensitive bi-polar gradient waveforms with a gradient echo imaging pulse sequence to increase the sensitivity to lesion detectability. The bi-polar gradients generate a broad distribution of velocities in a large voxel. Relevant stenoses present in a voxel will result in intra-voxel flow dephasing in voxels immediate to and distal to the stenosis. After identifying a stenosis, a second MR image, having a higher resolution than the first, is used to grade the stenosis.

44 Claims, 9 Drawing Sheets

OTHER PUBLICATIONS

Ho KY, Leiner T, de Haan MW, Kessels AG, Kitslaar PJ, and van Engelshoven JM. Peripheral vasculature tree stenoses: evaluation with moving–bed infusion–tracking MR angiography. *Radiology* 1998; 206:683–92.

Meaney JF, Ridgway JP, Chakraverty S, Robertson I, Kessel D, Radjenovic A, Kouwenhoven M, Kassner A, and Smith MA. Stepping–table gadolinium–enhanced digital subtraction MR angiography of the aorta and lower extremity arteries: preliminary experience. *Radiology* 1999; 211: 59–67.

Foo, TKF, Saranathan M, Prince MR, and Chenevert TL. Automated detection of bolus arrival and initiation of data acquisition in fast, three–dimensional, gadolinium–enhanced MR angiography. *Radiology* 1997; 203: 275–80.

Wilman AH, Riederer SJ, Huston J. $3^{rd}$, Wald JT, and Debbins JP. Arterial phase carotid and vertebral artery imaging in 3D contrast–enhanced MR angiography by combining fluoroscopic triggering with an elliptical centric acquisition order. *Magn. Reson Med.* 1998; 40: 24–35.

Riederer SJ, Fain SB, Kruger DG, and Busse RF. 3D contrast–enhanced MR angiography using fluoroscopic triggering and an elliptical centric view order. *Int. J. Card Imaging* 1999; 15: 117–29.

Prince MR, Chenevert TL, Foo TKF, Londy FJ, Ward JS, Maki JH. Contrast enhanced abdominal MR angiography: Optimization of imaging delay time by automating the detection of contrast material arrival in the aorta. *Radiology* 1997; 203: 109–114.

Meany, Dr. James FM, Leeds General Infirmary, Leeds, UK Moving Bed MRA, The Future of Peripheral Arteriography? *Phillips*.

Kouwenhoven, M., MRA with moving bed imaging, IX International Workshop on Magnetic Resonance Angiography and Introductory Course "New Horizons on MRA and CTA", Valencia, Oct. 7–11, 1997, Book of Abstracts, *The MR Angio Club*, p. 158.

\* cited by examiner

METHOD AND APPARATUS FOR EFFICIENT STENOSIS IDENTIFICATION IN PERIPHERAL ARTERIAL VASCULATURE USING MR IMAGING

BACKGROUND OF THE INVENTION

The present invention relates generally to the art of locating a blood vessel lesion in a human subject, and more particularly, to an apparatus and method to efficiently identify a lesion over an entire patient's peripheral arterial vasculature and grade any identified stenosis using magnetic resonance imaging (MRI) technology.

Arteries are the blood vessels emanating from the heart that supply the necessary nutrients to the organs and tissues of the human body. A narrowing or constriction of an artery reduces the delivery of nutrients, such as oxygen to the recipient tissue and has profound effects on tissue function. In general, significant narrowing of an artery leads to compromised function of the organ in question, at best, and organ failure or death at worst. Stenosis or narrowing at any number of locations along the course of the arteries from the abdominal aorta through the calf can result in compromise of arterial blood flow to the distal lower extremities. The evaluation of the peripheral vessels is further complicated by the high incidence of tandem or synchronous lesions, any one of which could be the underlying cause for diminished arterial blood flow. Furthermore, the surgical decisions for potential bypass procedures to improve distal blood flow are greatly affected by the ability to assess the arteries in the foot. As a result, the successful imaging of the lower extremities (i.e. the peripheral run-off study) requires not only the accurate assessment of the presence and functional significance of a narrowing, but also the ability to evaluate the entire arterial course of the peripheral arterial tree from abdominal aorta to the foot. It is known that the flow in the vessel at the point of narrowing and immediately after the narrowing is characterized by rapid flow velocities and/or complex flow patterns. Quantitative flow data can readily aid in the diagnosis and management of patients and also help in the basic understanding of disease processes.

There are many techniques available for the assessment of the peripheral arteries that include traditional invasive catheter angiography and ultrasound. Because conventional x-ray angiography requires catheterization and the use of nephrotoxic iodinated contrast agents, it is reserved as the final option. Screening for peripheral arterial occlusive disease (PAOD) is typically performed using non-invasive methods such as ultrasound or plethysmography. However, neither of these techniques can provide angiographic illustration of the vessels and merely provides the assessment of individual segments of the intervening arterial anatomy. Both techniques are operator dependent and have confounding technical difficulties which make the imaging often tedious to perform. Moreover, neither technique can provide the comprehensive information required for surgical planning and traditional x-ray angiographic depiction is generally required as an adjunct for pre-operative management.

Magnetic resonance angiography (MRA) is an emerging method for the non-invasive assessment of arteries. Up to now, the application of MRA has been tailored to individual smaller vascular territories (40–50 cm fields of views). With the ability now to translate the table and imaging multiple overlapping fields-of-view, MRA can now be prescribed to image a much larger area such as necessary for evaluation of PAOD. The use of intravenously administered contrast agents for contrast-enhanced MRA, in particular, has enabled the depiction of 1–1.2 meters of arterial anatomy in less than 1 minute. MRA can also be performed using a number of methods. One technique, phase contrast (PC) MRA is a practical and clinically applicable technique for imaging blood flow. MRI utilizes radio frequency pulses and magnetic field gradients applied to a subject in a strong magnetic field to produce viewable images. When a substance containing nuclei with net nuclear magnetic moment, such as the protons in human tissue, is subjected to a uniform magnetic field (polarizing field $B_0$), the individual magnetic moments of the spins in the tissue attempt to align with this polarizing field (assumed to be in the z-direction), but precess about the direction of this magnetic field at a characteristic frequency known as the Larmor frequency. If the substance, or tissue, is subjected to a time-varying magnetic field (excitation field $B_1$) applied at a frequency equal to the Larmor frequency, the net aligned moment, or "longitudinal magnetization", $M_Z$, may be nutated, or "tipped", into the x-y plane to produce a net transverse magnetic moment $M_t$. A signal is emitted by the excited spins after the excitation signal $B_1$ is terminated (as the excited spins decays to the ground state) and this signal may be received and processed to form an image.

When utilizing these signals to produce images, magnetic field gradients ($G_x$, $G_y$ and $G_z$) are employed. Typically, the region to be imaged is scanned by a sequence of measurement cycles in which these gradients vary according to the particular localization method being used. The resulting MR signals are digitized and processed to reconstruct the image using one of many well-known reconstruction techniques.

Phase contrast MRA makes use of flow encoding gradient pulses which impart a velocity-dependent phase shift to the transverse magnetization of moving spins while leaving stationary spins unaffected (Moran P. R. A Flow Velocity Zeugmatographic Interlace for NMR Imaging in Humans. Magnetic Resonance Imaging 1982; 1: 197–203). Each phase contrast acquisition generates two images: a magnitude image that is proportional to the proton density of the object and may also be $T_1$-weighted, and an image representing the phase of the object. The phase image produced has information only from the moving spins and the signal from stationary tissue is suppressed. Images representing both the average flow velocity over the entire cardiac cycle and at a series of individual points in the cycle have been generated using this technique. The phase contrast MR method produces phase images with intensities that represent the magnitude of the flow velocity and also the direction of flow. Therefore, such images may be used for both qualitative observation of blood flow and quantitative measurement. The practical application of phase contrast MR angiography and venography to the quantitative determination of flow velocity is therefore evident.

It would be advantageous to use magnetic resonance imaging technology to efficiently locate and identify a stenosis in a blood vessel along a patient's peripheral arterial vasculature and use this MR technology to grade the stenosis for follow up care. It would also be advantageous to use a contrast agent bolus injection to increase the image signal-to-noise ratio in the arterial vessels during the first passage of the contrast material to enhance the screening technique. However, to do so, a multi-station acquisition sequence must be used to scan the entire peripheral vasculature as the contrast bolus travels through the body. Previous attempts at using MR technology to improve the ability to detect and grade peripheral arterial stenoses have relied primarily on using a single anatomic scan to visualize the location of a stenotic vessel segment. In this method, it was desirable to achieve the highest spatial resolution possible by decreasing pixel size. In addition, in order to minimize flow-related artifacts such as intravoxel dephasing that can overestimate the degree of stenosis, the prior art employed first moment gradient nulling for flow compensation and short echo time (TE) parameters.

It would be desirable to improve on this prior art by accomplishing the converse. That is, to utilize the presence of flow-related artifacts to improve the detection of an arterial stenosis by sensitizing the image acquisition to intra-voxel flow dephasing effects, thereby exacerbating flow voids and increasing the conspicuity of arterial lesions in a quick screening scan. It would also be advantageous to have a method and apparatus for efficient visualization of a stenosis (i.e. lesions or narrowings) using MR technology for screening patients, followed with a more thorough and lengthy exam of the individual stenoses, enabling a more time-efficient examination. It would also be advantageous to use a contrast agent bolus injection to increase the image signal-to-noise ratio in the arterial vessels during the first passage of the contrast material to enhance the screening technique. However, to do so a multi-station acquisition sequence must be used to scan the entire peripheral vasculature as the contrast bolus travels through the body.

SUMMARY OF THE INVENTION

The present invention relates to a method and apparatus for efficient stenosis identification in peripheral arterial vasculature using MR technology, that solves the aforementioned problems.

The present invention includes a two step approach to accurately identify any blood vessel lesions and then if a lesion is found, specify the degree of stenosis. In the initial step, an examination for lesion identification is disclosed that includes tracking a contrast bolus as it passes through the arterial vasculature of a patient and acquiring a series of low spatial resolution MR images as the contrast bolus travels through the patient's vasculature. Preferably, the MR image is acquired using a gradient echo imaging pulse sequence with a flow sensitive bi-polar gradient waveform. The bi-polar gradients generate a broad distribution of velocities in a large voxel. Since a stenosis present in a given voxel will result in intra-voxel flow dephasing in voxels immediate to and distal to the stenosis, a stenosis can be quickly and efficiently localized using the initial step. After a stenosis is identified, a second step is performed in which a high spatial resolution MR image is acquired for more accurate and specific grading of the stenosis in a targeted area.

According to one aspect of the invention, a method of identifying a stenotic vessel in a patient's peripheral arterial vasculature using MR imaging is disclosed which includes tracking passage of a contrast bolus through the patient and simultaneously performing a screening study by acquiring a series of first, fast MR images having a low spatial resolution along the patient's peripheral arterial vasculature as the contrast bolus passes through the patient to scan for a suspected stenosis. The method next includes scanning the series of first MR images to identify a suspected stenosis, then performing a detailed study by acquiring a second MR image having a higher resolution than the series of first MR images for grading the identified stenosis.

In accordance with another aspect of the invention, an examination method is disclosed to identify a lesion in a blood vessel of a patient's peripheral arterial vasculature and grade a stenosis resulting therefrom. The examination includes first scanning the peripheral vessels, for example using contrast-enhanced MRA based on gradient echo imaging pulse sequence having a flow sensitizing bi-polar gradient waveform across a patient's peripheral arterial vasculature, and then detecting and localizing a suspected stenosis using the series of first MR images. The method next involves acquiring a second MR image if a stenosis is detected and localized. The second MR image has a higher resolution than the series of first MR images and is acquired in a region in which the suspected stenosis is detected and localized to grade the suspected stenosis. If a stenosis is not detected and localized, the examination is ended without further MR image acquisitions.

In accordance with another aspect of the invention, an MRI apparatus is disclosed to conduct MR stenosis screening, and if necessary, grade a stenotic vessel that includes an MRI system having a number of gradient coils positioned about a bore of a magnet to impress a polarizing magnetic field, an RF transceiver system, and an RF modulator controlled by a pulse control module to transmit RF signals to an RF coil assembly in order to acquire MR images. The MRI apparatus also includes a computer programmed to operate the MRI system in two modes of operation to efficiently conduct a stenosis exam across an entire patient's peripheral arterial vasculature. The first mode is programmed to acquire a series of first MR images with low resolution over the patient's peripheral arterial vasculature, then receive an input to either end the stenosis exam or switch to a second mode of operation if a stenosis is indicated in the series of first MR images. In the second mode of operation, the computer is programmed to localize a field-of-view (FOV) to target the stenosis, and then acquire at least one second MR image with resolution higher than that of the series of first MR images of the localized FOV.

In accordance with yet another aspect of the invention, the aforementioned methods are implemented in a computer program that is fixed on a computer readable storage medium that, when executed, causes the computer to acquire a series of first MR images of a patient's peripheral arterial vasculature. Each of the first MR images in the series of first MR images is acquired within a scan station as a contrast bolus travels therethrough. The series of first MR images has high phase cancellation to screen a patient for possible arterial lesions. The computer is further programmed to limit a FOV to a target region within the patient's peripheral arterial vasculature if a lesion is located, and then acquire a second MR image of the targeted region. The second MR image having a resolution higher than that of the series of first MR images, and only being acquired if the series of first MR images indicates the presence of a lesion, or stenosis.

In this manner, the higher resolution targeted acquisition near the site of interest is performed only if a lesion is present to effectively grade the stenosis. This technique provides a two-step technique involving a first step with increased sensitivity to detect lesions that can be acquired quickly, across the entire peripheral arterial vasculature and then only performing the more time-consuming second step of acquiring an image with high specificity for grading the lesion only if one is detected in the first step. This two-tiered approach increases the efficiency for accurate peripheral vasculature stenosis detection and assessment.

Various other features, objects and advantages of the present invention will be made apparent from the following detailed description and the drawings.

BRIEF DESCRIPTION OF THE DRAWINGS

The drawings illustrate the best mode presently contemplated for carrying out the invention.

In the drawings.

DETAILED DESCRIPTION OF THE PREFERRED EMBODIMENT

Figure 1:
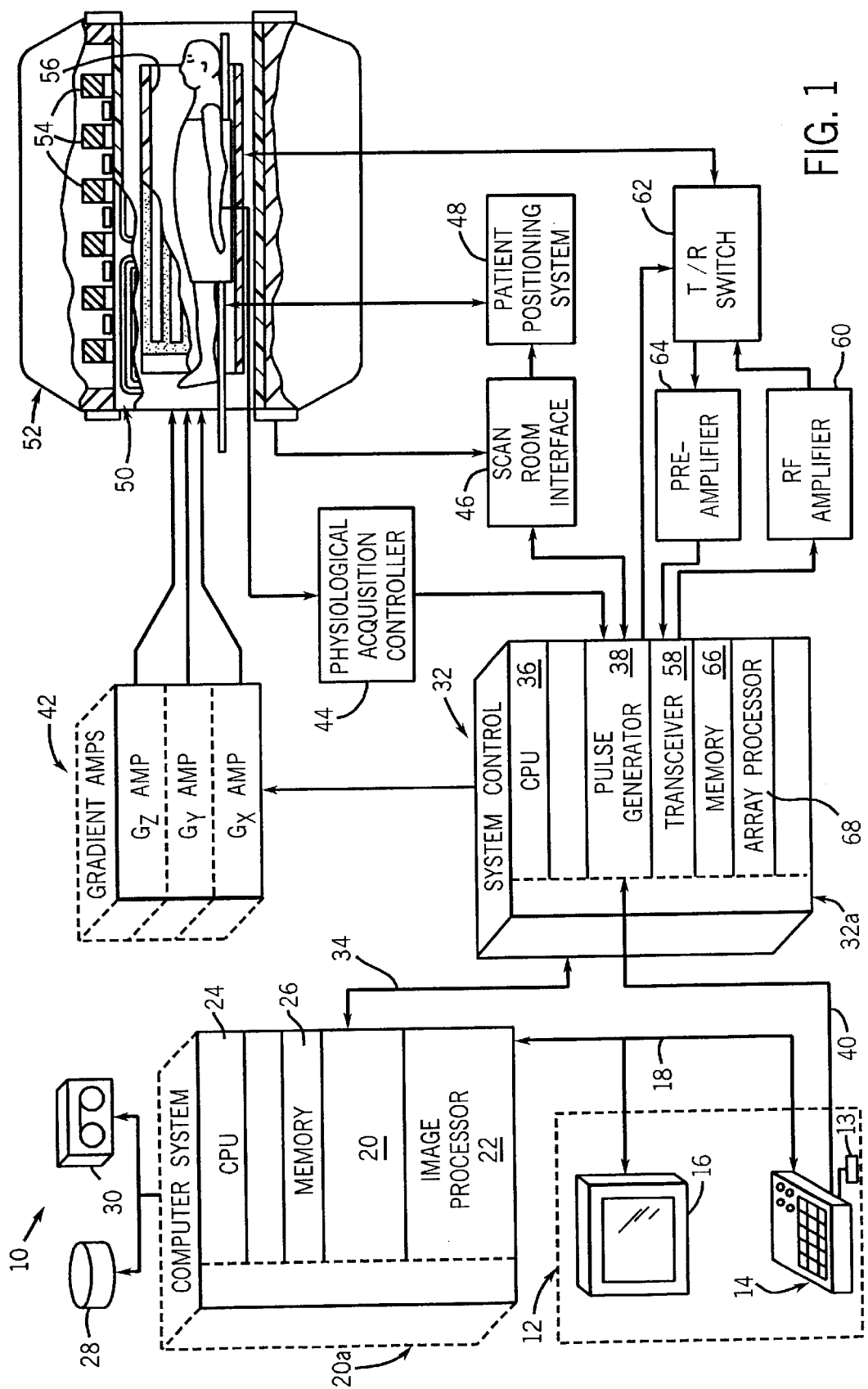
FIG. 1 is a schematic block diagram of an MR imaging system for use with the present invention.

Referring to FIG. 1, the major components of a preferred MRI system 10 incorporating the present invention are shown. The operation of the system is controlled from an operator console 12 which includes a keyboard or other input device 13, a control panel 14, and a display 16. The console 12 communicates through a link 18 with a separate computer system 20 that enables an operator to control the production and display of images on the screen 16. The computer system 20 includes a number of modules which communicate with each other through a backplane 20a. These include an image processor module 22, a CPU module 24 and a memory module 26, known in the art as a frame buffer for storing image data arrays. The computer system 20 is linked to a disk storage 28, a tape drive 30, or any other form of computer readable storage medium for storage of image data and programs, and it communicates with a separate system control 32 through a high speed serial link 34. The input device 13 can include a mouse, joystick, keyboard, track ball, touch screen, light wand, voice control, or similar device, and may be used for interactive geometry prescription.

The system control 32 includes a set of modules connected together by a backplane 32a. These include a CPU module 36 and a pulse generator module 38 which connects to the operator console 12 through a serial link 40. It is through link 40 that the system control 32 receives commands from the operator which indicate the scan sequence that is to be performed. The pulse generator module 38 operates the system components to carry out the desired scan sequence and produces data which indicates the timing, strength and shape of the RF pulses produced, and the timing and length of the data acquisition window. The pulse generator module 38 connects to a set of gradient amplifiers 42, to indicate the timing and shape of the gradient pulses that are produced during the scan.

The pulse generator module 38 also receives patient data from a physiological acquisition controller 44 that receives signals from a number of different sensors connected to the patient, such as ECG signals from electrodes attached to the patient. The pulse generator module 38 connects to a scan room interface circuit 46 which receives signals from various sensors associated with the condition of the patient and the magnet system. It is also through the scan room interface circuit 46 that a patient positioning system 48 receives commands to move the patient to the desired position for the scan.

The gradient waveforms produced by the pulse generator module 38 are applied to the gradient amplifier system 42 having $G_x$, $G_y$, and $G_z$ amplifiers. Each gradient amplifier excites a corresponding gradient coil in an assembly generally designated 50 to produce the magnetic field gradients used for spatially encoding acquired signals. The gradient coil assembly 50 forms part of a magnet assembly 52 which includes a polarizing magnet 54 and a whole-body RF coil 56. A transceiver module 58 in the system control 32 produces pulses which are amplified by an RF amplifier 60 and coupled to the RF coil 56 by a transmit/receive switch 62. The resulting signals emitted by the excited nuclei in the patient may be sensed by the same RF coil 56 and coupled through the transmit/receive switch 62 to a preamplifier 64. The amplified MR signals are demodulated, filtered, and digitized in the receiver section of the transceiver 58. The transmit/receive switch 62 is controlled by a signal from the pulse generator module 38 to electrically connect the RF amplifier 60 to the coil 56 during the transmit mode and to connect the preamplifier 64 during the receive mode. The transmit/receive switch 62 also enables a separate RF coil (for example, a surface coil) to be used in either the transmit or receive mode.

The MR signals picked up by the RF coil 56 are digitized by the transceiver module 58 and transferred to a memory module 66 in the system control 32. When a scan is completed, an array of raw k-space data has been acquired in the memory module 66. This raw k-space data is rearranged into separate k-space data arrays for each image to be reconstructed, and each of these is input to an array processor 68 which operates to Fourier transform the data into an array of image data. This image data is conveyed through the serial link 34 to the computer system 20 where it is stored in the disk memory 28. In response to commands received from the operator console 12, this image data may be archived on the tape drive 30, or it may be further processed by the image processor 22 and conveyed to the operator console 12 and presented on the display 16.

The present invention includes a method and system suitable for use with the above-referenced MR system, or any similar or equivalent system for obtaining MR images. The present invention is a two-tiered technique to improve the efficiency for accurate peripheral vasculature stenosis identification and grading.

Figure 2:
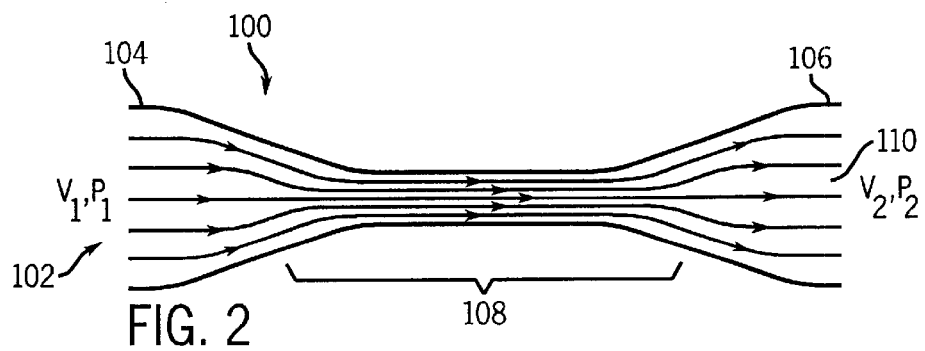
FIG. 2 is a schematic representation of an exemplary stenotic vessel in a human patient for which the present invention is directed at locating.

Referring to FIG. 2, a schematic representation of a blood vessel 100 is shown longitudinally with viscous blood 102 flowing therethrough. The blood vessel 100 is shown with a first end 104 acting as an inlet, and a second end 106 acting as an outlet. Between ends 104 and 106 is a constriction, or a stenotic area 108. In such a stenotic vessel, blood flow velocity $V_2$ at the outlet end 106 is greater than the blood flow velocity $V_1$ at the inlet at 104 (i.e., $V_2 > V_1$), and, correspondingly, the blood pressure $P_2$ at the outlet end 106 is less than the blood pressure $P_1$ at the inlet end 104 (i.e., $P_2 < P_1$). In general, in a stenotic vessel, such as blood vessel 100, the region 110 within the outlet end of the vessel 106, which is immediately downstream from the constriction 108, is characterized by having rapid blood flow velocities, or complex blood flow patterns. Furthermore, in regions where the degree of constriction is high, the emerging flow patterns in region 110 cease to be laminar and take on complex flow patterns, including the generation of flow vortices or eddys.

The present invention, in part, takes advantage of the fact that hemodynamically significant stenoses can be characterized by the high velocity gradients across the flow axis, and along its length. The hemodynamic severity of the stenosis can then be graded by the changes in the velocity gradients through the stenotic area. In general, the present invention is a two-tiered approach to identifying a stenotic vessel, or a region having a lesion on a blood vessel, then if needed, grading the stenosis with a more detailed image acquisition. This approach increases the efficiency for accurate stenosis detection and assessment in that by first acquiring a low spatial resolution image (e.g., 1–2 mm. pixel) that is highly sensitive to lesion detection, a large region can be initially scanned quickly, and if a lesion is identified, a second scan of higher spatial resolution can be acquired for more accurate and specific grading of the stenosis.

Figure 3:
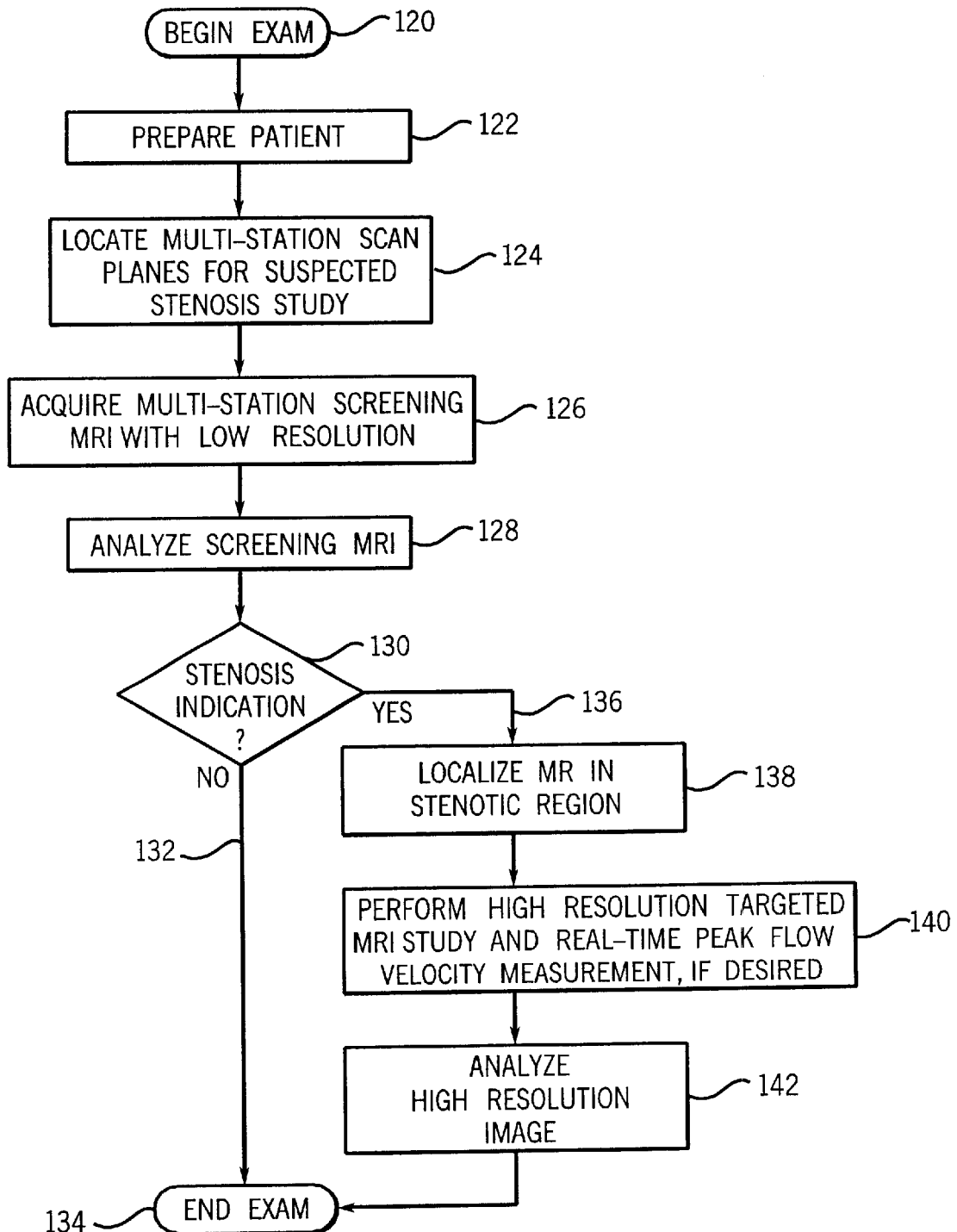
FIG. 3 is a flow chart illustrating an embodiment of the present invention.

FIG. 3 is a flow chart showing an embodiment of the present invention that depicts both the method and a representation of the software programmed into the computer of the MRI apparatus of FIG. 1. The scan begins with an initialization 120 that includes patient preparation 122 to undergo an MRI exam. Such preparation includes proper placement of the patient on a movable table, as will be described in detail with reference to FIG. 8, and injecting a contrast agent bolus to provide an increased signal-to-noise ratio in the arterial vessels during the first pass of the contrast material. In the first step of the two-tiered system of the present invention, a screening study is conducted for a fast screen that is applicable with both extra-cellular contrast agents and intravascular contrast agents. In order to effectively and efficiently image the peripheral arterial vasculature of a patient, a flow sensitive three-dimensional fast imaging pulse sequence is used. Since the peripheral vasculature can cover a 1–1.2 meter length of the body, the present invention uses a multi-station fast three-dimensional pulse sequence that is able to follow, or pursue, the passage of the contrast bolus as it passes through the body, as will be further described with reference to FIGS. 8–11. In accordance with that process, in general, the technique periodically inspects for contrast arrival in each subsequent station in a multi-station arrangement using, for example, an elliptical centric view acquisition order. Once contrast has arrived at a subsequent station, image acquisition is suspended and the table is automatically moved to the next station. Preferably, the three-dimensional gradient acquisition sequence used in this technique utilizes approximately 2×3×4 mm. voxel dimensions with a partial Fourier acquisition technique acquiring approximately 96 $k_y$ lines and about 32 $k_z$ lines. Using a repetition time of approximately 3–5 sec., and assuming that one echo is acquired for each RF pulse, a total of 3072 RF excitation pulses are used for each acquisition. As a result, a complete image can be acquired with a total scan time of approximately 15 seconds. As will be further described with reference to FIG. 4, flow sensitizing gradients are applied in all three directions to provide insensitivity to orientation of the vessel or stenosis. However, in the distal peripheral vasculature where the flow is predominately in the cranial-caudal (superior-inferior) direction, the flow sensitizing gradients can be applied in only one direction.

Referring back to FIG. 3, after the patient is prepared 122, the multi-station study is planned and scout scans are acquired. The multi-station scan planes for the stenosis study are located 124 for the peripheral arterial vasculature of the patient. Next, a series of first MR images having low resolution are acquired to screen the scan planes 126. The series of first MR images are acquired using a pulse sequence with flow sensitizing bi-polar gradients, as will be further described with reference to FIG. 4. The series of first MR images are then analyzed at 128 for an indication of a lesion, or a stenosis, by looking for flow voids as an indication of the stenosis. The flow voids are generated close to or around the site of a stenosis as a result of applying the flow sensitizing bi-polar gradient waveform in all three directions in the pulse sequence. If there are no indications of flow voids 130, 132, and therefore, no indication of a stenosis, the exam is considered completed 134, and the patient released without further time consuming MR image acquisitions. In this manner, patients can be more efficiently screened for complete peripheral arterial vasculature stenosis detection.

However, if a stenosis is indicated 130, 136, by the appearance of flow voids in at least one of the series of first MR images, the field-of-view (FOV) is limited to a target region of the suspected stenosis 138. Next, a second MR image is acquired having a higher resolution than the series of first MR images to scan the identified suspected stenosis within the targeted, localized region 140. In addition, the severity of the stenosis can be assessed by measuring the velocity encoding (VENC) value in real-time such that the onset of complete intra-voxel flow dephasing is observed for an acquisition with large voxel sizes, or the onset of aliasing within the vessel for acquisitions with small voxel sizes, as will be further described with reference to FIGS. 5–7. The high resolution image is then analyzed 142 to grade the stenosis, after which, the exam is complete 134. This then provides a method and system for increasing the sensitivity to detect lesions, and also a method and system that has high specificity for grading a lesion, not with a single acquisition, but with a series of acquisitions.

Figure 4:
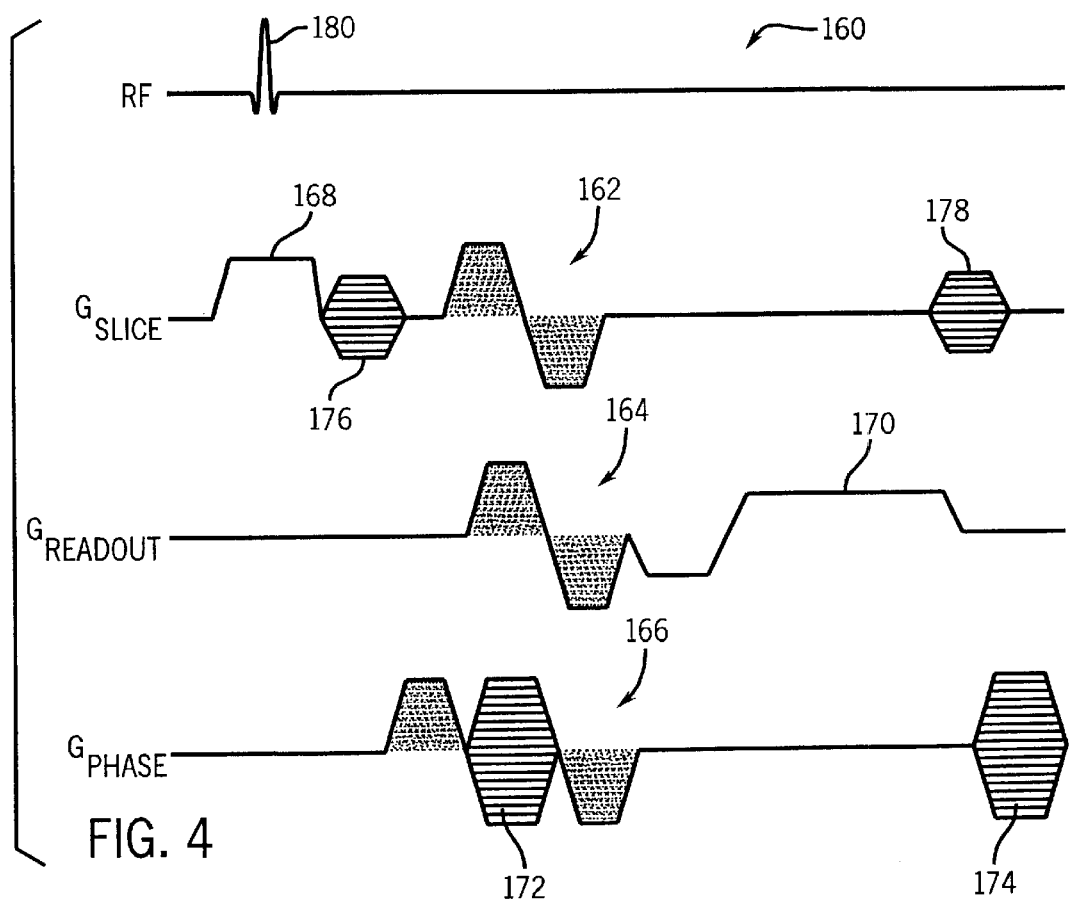
FIG. 4 is a timing diagram of an MR imaging pulse sequence used in the invention.

FIG. 4 shows the phase contrast imaging pulse sequence 160 used in acquiring the series of first MR images. As shown in this preferred embodiment, the flow sensitizing gradients 162, 164, and 166 create a flow sensitive pulse sequence that behaves as a screening tool with high sensitivity to the detection of lesions. The flow sensitizing gradients 162, 164, and 166 are bi-polar gradients to accentuate phase cancellation and thereby increase flow dephasing. Alternatively, the flow dephasing in the series of first MR images can be accomplished by increasing the voxel size for greater distribution of the velocity vectors. In either case, the first (screening) MR images acquired with high phase cancellation and low resolution, and therefore are acquired relatively fast. Generally, the first screening study can be accomplished with either a flow sensitive pulse sequence, as shown in FIG. 4, or with a contrast material enhanced imaging pulse sequence. The pulse sequence can be either a two-dimensional breath-held acquisition or a three-dimensional free-breathing acquisition that is respiratory-gated using a navigator echo, or similar respiratory gating technique.

As shown in FIG. 4, the flow sensitizing bi-polar gradients 162, 164, and 166 are applied in all three directions to provide insensitivity to orientation of the blood vessel, or the stenosis. It is understood that although FIG. 4 shows the flow sensitizing gradients substantially aligned, since this aspect of the present invention is not directed to measuring flow velocity, they need not be coincident. It is merely preferred that the flow sensitizing gradients 162, 164, and 166 be located between the pulse encoding gradient 168 and the readout gradient 170. The phase encoding gradients 172 and 174, along with the gradient crushers 176, 178 and the RF pulse 180 are each shown as reference points. Although the flow sensitizing gradient 166 in the phase direction is shown separated by the phase encoding gradient 172, it is understood that this is a preferred embodiment to increase flow sensitivity. Alternatively, each pole of the bi-polar gradient 166 can be brought closer together in time with a corresponding increase in amplitude of the first moment. As will become apparent, either a larger moment, or an increased temporal separation is needed to dephase the spins and increase flow sensitivity. In a preferred embodiment, the pulse sequence is a three-dimensional fast gradient echo pulse sequence using the bi-polar, flow sensitizing gradients 162, 164, 166.

The value of the first moment of the bi-polar gradient is nominally set to a low VENC value so that the velocity distribution within a voxel is greater than $2\pi$. This results in a cancellation of signal from that voxel as the net magnetization averages to zero, or close to zero.

Next, a brief summary description of the VENC value calculation and setting is explained. The value of the first moment for a single bi-polar gradient waveform is given by:

$$M_1 = AT,\qquad [1]$$

where A is the area of the uni-polar part of a bi-polar gradient waveform, and T is the temporal separation between the two uni-polar lobes, each having opposite polarity, that constitute the bi-polar gradient waveform, as shown in FIG. 4. The resulting phase generated by the bi-polar gradient waveform is given by:

$$\phi = \gamma M_1 \vec{v},\qquad [2]$$

where $\gamma$ is the gyromagnetic ratio and $\vec{v}$ is the velocity. The phase that is measured in phase-difference processing is given by:

$$\Delta\phi = 2\gamma M_1 \vec{v}.\qquad [3]$$

According to the present invention however, since the VENC value is such that at that particular velocity, the corresponding phase shift is $\pi$ radians, the first moment of the bi-polar waveform is adjusted such that:

$$M_1 = \frac{\pi}{\gamma VENC}.\qquad [4]$$

As is evident from comparing Eqns. 3 and 4, this expression for the VENC value is one-half that used in a phase contrast acquisition where the phase difference between two acquisitions, with toggled polarity of the bi-polar waveforms, determines the value for the first moment.

Figure 5:
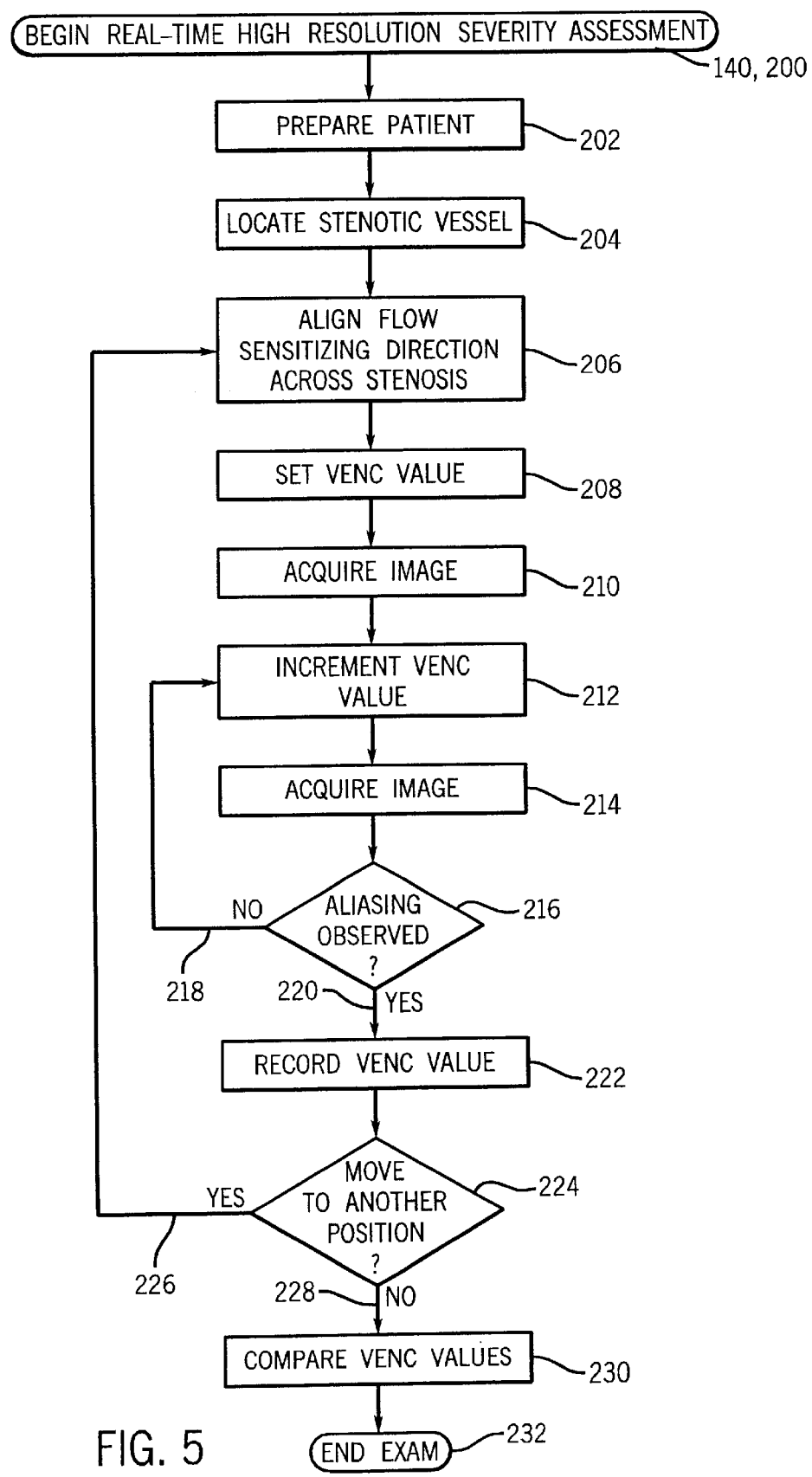
FIG. 5 is a flow chart illustrating one technique for assessing the severity of a stenosis once detected according to the present invention.

Referring now to FIG. 5, a detailed description of the real-time peak flow velocity measurement referred to in block 140 of FIG. 3 will now be described. It is this part of the invention that takes advantage of the fact that hemodynamically significant stenosis can be characterized by the high velocity gradients across the flow axis, and along the length of the stenosis. This aspect of the invention can be used to grade the stenosis based on the changes in the velocity gradients through the stenotic area. To do so, a real-time phase contrast MR image pulse sequence with phase difference processing is used to evaluate the peak flow velocity across such a stenosis. Thus, the user is allowed to control a direction of a velocity encoding gradient and a value of the velocity encoding gradient, hereinafter referred to as the VENC value. In general, by increasing the VENC value until an onset of flow related aliasing is observed, the peak velocity across the stenosis can be determined by correlating the onset of flow velocity aliasing with the VENC setting. The administration of a contrast agent shortens the $T_1$ time to improve the signal intensity, and consequently, increase the signal-to-noise ratio. This will result in a corresponding increase in the effectiveness of assessing the severity of the stenosis according to the present invention.

In accordance with this aspect of the invention, FIG. 5 depicts both the method and a representation of the software programmed into the computer of the MRI apparatus of FIG. 1. Upon initialization of the severity assessment routine 140, 200, a patient is prepared 202 to undergo an MRI exam, as is well known. The patient and/or the MR apparatus are situated so as to acquire the second MR images in a target area of a suspected stenotic vessel 204. Using the real-time phase contrast pulse sequence, as previously mentioned and will be further described with reference to FIG. 6, the flow sensitizing direction is aligned along the direction or axis of flow and across the stenosis at 206. At this point, the VENC value 208 is set to a value below which it is known that flow velocity aliasing will not occur, or an image can be acquired to set the VENC value where no aliasing is observed. FIG. 7 shows an example of such flow related aliasing. FIG. 7 is a cross-section of the vessel 100, such as that shown in FIG. 2. Without any flow related aliasing, the vessel 100 will appear as a white-out in the reconstructed MR image as depicted by reference number 262. The phase within the vessel is also smoothly varying. However, after the onset of flow related aliasing (which will be described mathematically in more detail hereinafter), aliasing section 264 appears darkened, either in shades of gray or in black. Aliasing section 264 may appear as an entire portion of the vessel 100, as shown in FIG. 7, or may appear as a strip or smaller section of the vessel 100. In addition, the onset of flow related aliasing can be characterized by the abrupt changes in the phase within the vessel. In any case, when the VENC value is increased to the aliasing point, there will be some indication of sudden graying within the vessel.

Referring back to FIG. 5, once the VENC value is set 208, an image is acquired 210, the VENC value is increased 212, and another image is acquired 214. That image is then used to determine whether flow related aliasing has occurred in the stenotic vessel 216. If it has not 218, the VENC value is incrementally increased 212 until flow related aliasing is observed 216, 220 in the image acquired at 214. The VENC value 212 which resulted in the onset of flow related aliasing 216, 220 is then recorded at 222. If it is desired to acquire another set of data in a different position along the stenotic vessel 224, the acquisition site is relocated along the stenotic vessel 226, and the aforementioned process is repeated as many times as desired by the MR operator. That is, the spins are again aligned along the flow sensitizing direction across the stenosis 206, the VENC value is reset at 208, an image is acquired at 210, and then the VENC value is incremented 212 until aliasing is observed 216, 220 in the acquired image 214. After the VENC value is again recorded 222, and the MR operator has acquired sufficient data 224, 228, the correlated VENC values can then be compared 230 in order to determine the severity of the stenosis and/or the exact location of the stenosis. The exam is then complete 232.

Figure 6:
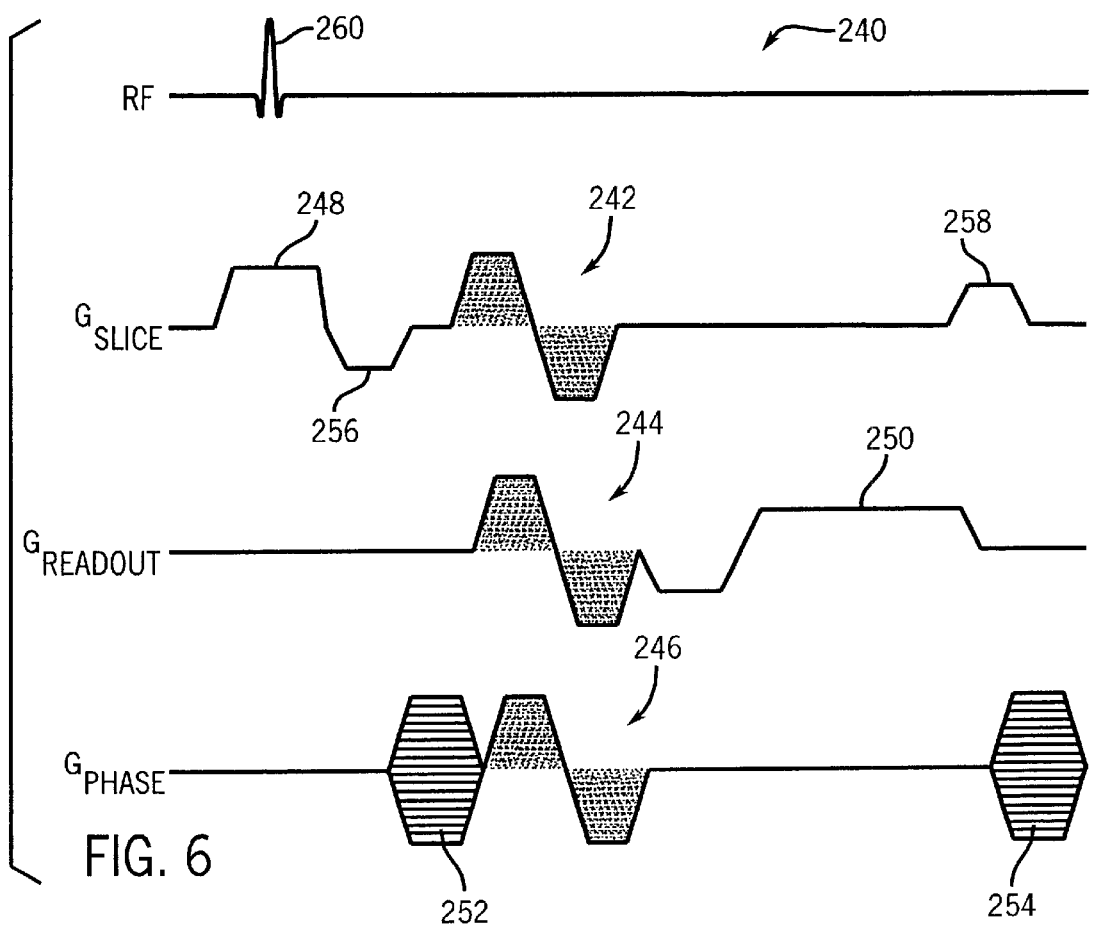
FIG. 6 is a timing diagram of an MR imaging pulse sequence used in accordance with the flow chart of FIG. 5.
Figure 7:
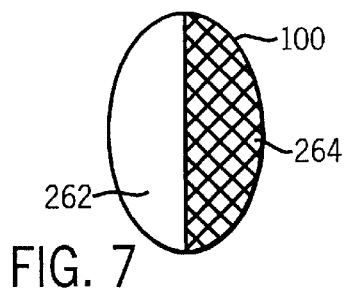
FIG. 7 is a schematic representation of a cross-section of a blood vessel showing flow velocity aliasing in accordance with the technique illustrated in FIGS. 5 and 6.

FIG. 6 shows the phase contrast imaging pulse sequence 240 used in the present 20 invention. As shown in this preferred embodiment, the flow sensitizing gradients 242, 244, and 246 are relatively coincident in time to allow the direction of the flow sensitizing gradients to be rotated in real-time by the user. It is understood that although FIG. 6 shows the flow sensitizing gradients substantially aligned, the importance of the placement of the flow sensitizing gradients is that they be relatively coincident with respect to the overall pulse sequence 240. It is preferred that the flow sensitizing gradients 242, 244, and 246 be located relatively coincident in time between the pulse encoding gradient 248 and the readout gradient 250. The phase encoding gradients 252 and 254, along with the gradient crushers 256, 258 and the RF pulse 260 are each shown as reference points.

The following description is a more complete explanation of bi-polar gradients and phase contrast imaging. Considering a magnetic field gradient applied in a specific direction, the phase accumulated by a spin ensemble is a function of the equation of motion of that ensemble and the applied gradient field. That is:

$$\phi = \int_0^t \gamma \vec{G}(t) \cdot \vec{r}(t) dt, \quad [5]$$

where $\vec{G}(t)$ is the vector describing the time-varying gradient (direction and amplitude), and $\vec{r}(t)$ is the motion vector such that $$\vec{r}(t) = \vec{r}_0 + \vec{v} t + \tfrac{1}{2} \vec{a} t^2 + \quad [6]$$

with the first term representing the initial position of the spin ensemble at time t=0 and the other terms representing the motion due to a constant velocity, acceleration, and the higher orders of motion. The higher orders of motion can be ignored for this description since the constant velocity component predominates.

To have a better understanding of the interaction of velocity and phase, Eqn. [5] can be expanded as:

$$\phi = \gamma r_0 \int_0^t G(t) dt + \gamma v \int_0^t G(t) dt = \gamma r_0 M_0 + \gamma v M_1, \quad [7]$$

where $M_0$ and $M_1$ represent the zeroth and first gradient moments, respectively. If G(t) is a single, uni-polar gradient lobe, the phase in a volume element would be given by Eqn.[7]. If, immediately following this gradient, an identical uni-polar gradient is applied with opposite sign, the phase due to this second gradient lobe is given by:

$$\phi' = \gamma r_0 M_0' + \gamma v M_1'. \quad [8]$$

Since the zeroth moment is merely the area under the gradient lobe, $M_0'$ is equal to $-M_0$. When combined, the two uni-polar lobes of identical area, but of opposite sign, are essentially a single bipolar gradient waveform. However, as the first moment is an integral weighted by time, $M_1'$ does not equal $-M_1$. The phase accumulated by the combined bipolar gradient lobe is then the sum of Eqn.[7] and Eqn.[8], which is given by:

$$\phi_1 = \phi + \phi' = \gamma v (M_1' + M_1). \quad [9]$$

Note that the phase accumulation from an applied bipolar gradient is independent of initial position and is directly proportional to the velocity. The bipolar gradient has a zero net area and has no effect on stationary tissue. Thus, without any loss of generality, G(t) can be considered a single bipolar waveform, such that the phase is simply given by Eqn. [2]:

$$\phi = \gamma M_1 \vec{v} \quad [2]$$

In a perfect experiment, a single acquisition with a bipolar gradient will provide an image whose phase represents flow in the direction of the applied gradient as given by Eqn.[2]. However, residual eddy currents, magnetic field homogeneity, and magnetic susceptibility contribute to a spatially varying non-zero phase, even for stationary tissue. This spatial phase variation is not flow-related and can be large across an image. In order to avoid this problem, two images with bipolar gradients of opposite sign (toggled bipolar gradients) are subtracted. Any non-zero phase due to stationary tissue are canceled out, leaving an image with the difference in phase accumulated in the two acquisitions. By inverting the bipolar waveform for the second acquisition, the phase of this subsequent acquisition is the negation of Eqn.[2], (i.e., $\phi = -\phi_1$), and $M_{1,acq2} = -M_{1acq1} = -M_1$. The phase difference in the subtracted image is then:

$$\Delta\phi = \phi_1 - \phi_2 = \gamma \vec{v} \Delta M_1, \quad [10]$$

with $$\Delta M_1 = \int_0^t 2tG(t)dt. \quad [11]$$

From the phase difference equation, Eqn. [10], it is clear that if the spins reverse flow direction, i.e., $\vec{v}$ reverses sign, there is a corresponding change in the sign of $\Delta\phi$. Thus, the magnitude of a phase difference image provides a measure of the flow velocity, while the sign indicates flow direction.

The phase difference image (after subtraction) displays the value of Eqn. [10] at each pixel. The phase shift given by Eqn. [10] is proportional to velocity and the difference in the first gradient moment (Eqn.[11]). If $\Delta\phi$ exceeds π radians or 180°, or the misrepresentation of one phase as that of another different phase, aliasing occurs, as shown in FIG. 7. For example, a phase difference of +190° is indistinguishable from a phase difference of −170° or even −530°. Thus, spins with a high velocity may be represented as having a lower velocity or spins flowing in one direction may be incorrectly represented as flowing in the opposite direction. This is the phenomenon herein referred to as velocity flow aliasing and is analogous to image warp-around.

In order to find the point of flow related aliasing, the phase shifts in Eqn. [10] are first brought to within ±180° (±πradians). Then by dialing up the VENC value until the onset of flow related aliasing, the peak velocity can be determined as previously mentioned.

The invention also includes tracking passage of a contrast bolus through a patient while performing the screening study. FIGS. 8–11 describe the technique to acquire the series of first MR images simultaneously with the tracking of the contrast bolus.

Figure 8:
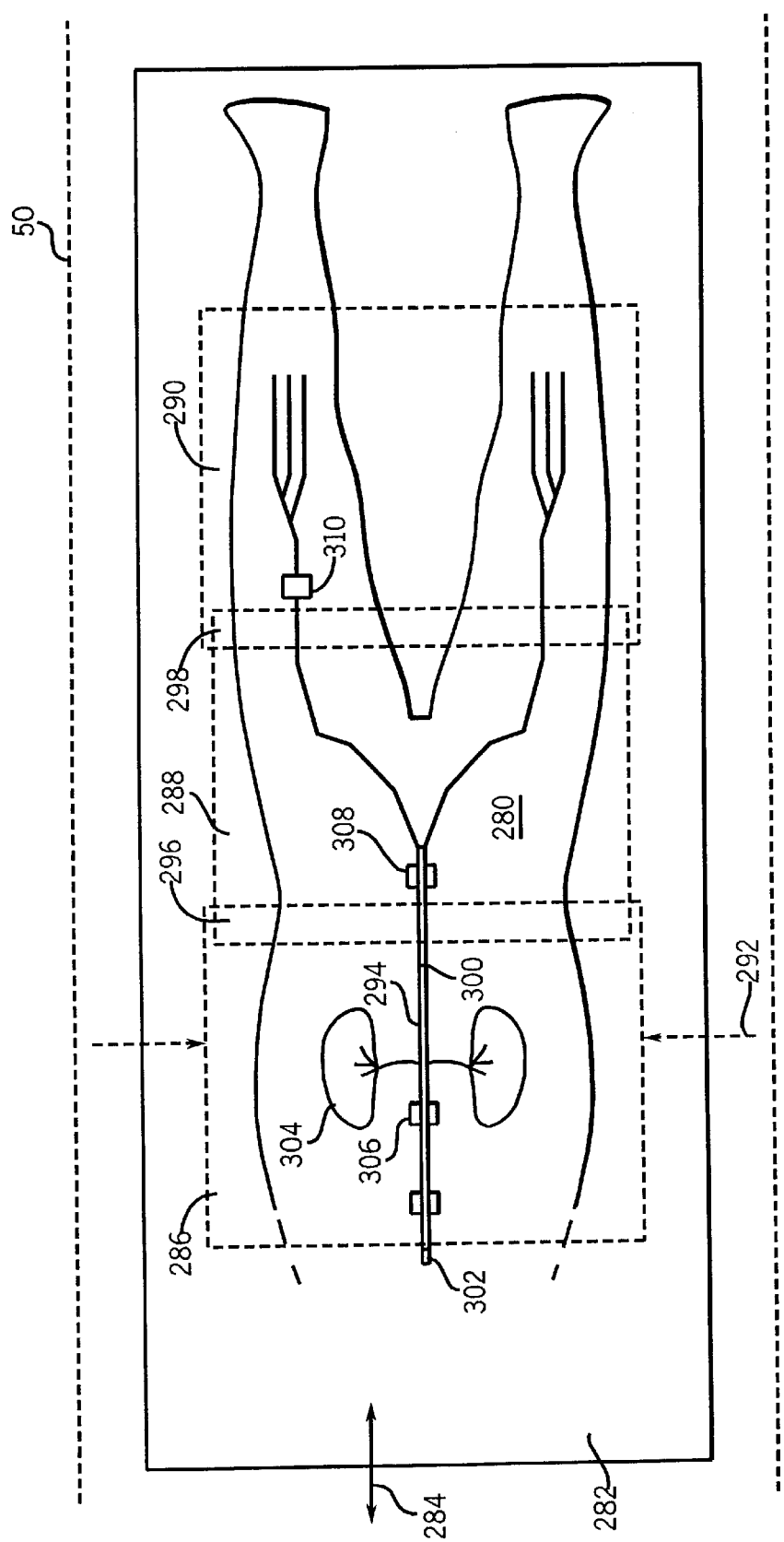
FIG. 8 is a schematic diagram illustrating an arrangement for conducting a peripheral MR angiography exam to locate and assess a stenosis in accordance with the present invention.

Referring now to FIG. 8, a patient 280 is shown supported on a computer controlled, movable table 282, which may be slid or translated fore and aft as indicated by arrow 284 in the magnet of MR apparatus 10. Thus, patient 280 may be selectively positioned within the bore of main magnet 50. The motion of the table is under computer control whose position along axis 284 of the magnet bore can be precisely controlled and is reproducible.

More specifically, FIG. 8 shows patient 280 having a blood vessel 294 of substantial length, such as the aorta, femoral arteries, or other artery, extending from the abdominal area into the lower limbs of the subject. It is desirable to acquire MR image data of vessel 294 in its entirety. However, because of the substantial length of vessel 294, it is necessary to obtain the data by establishing a plurality of scan locations or stations 286, 288, 290 along the length of patient 280 and within components of the MR system. Each scan station 286, 288, 290 includes a pre-defined section of patient 280. For example, scan station 286 includes the upper trunk area of patient 280, scan station 288 includes the lower trunk area, and scan station 290 includes the lower extremities of the patient 280. To acquire MR data associated with a particular scan station, movable table 282 is moved fore and aft along axis 284 to position the particular scan station in a specified relationship with the main magnet 50. For example, FIG. 8 shows the midpoint of scan station 286 positioned at isocenter 292 of magnet 50.

In a conventional arrangement, an entire set of MR data pertaining to the segment of vessel 294, lying within scan station 286, would be acquired while such scan station was in the position shown in FIG. 8. Then, table 282 would translate the patient 280 leftward, as viewed in FIG. 8, to position the midpoint of scan station 288 at isocenter 292. After scanning an entire set of data pertaining to the segment of vessel 294 within scan station 288, the patient 280 would be further translated, to position the midpoint of scan station 290 at isocenter 292. A set of MR data pertaining to scan station 290 would then be scanned to complete the data acquisition procedure. It is noted that a certain amount of over-lap 296, 298 may occur between adjacent scan stations. This is both desired and needed to enable the effective combination of images from each station into a single combined image covering the entire extent of the imaged region from all stations.

It is common practice in MR angiography to intravenously inject a contrast agent, such as 20–40 cc of gadolinium chelate, into the blood stream 300 flowing through vessel 294 which provides a bolus 302 to flow through the blood stream 300. Since vessel 294 carries blood from the upper body to the lower limbs of the patient 280, the flow direction is from left to right, as viewed in FIG. 8. After reaching the pulmonary system 306, the bolus 302 would arrive first at scan station 286, then arrive at scan station 288, and finally arrive at scan station 290.

In accordance with a conventional technique developed by the General Electric Company known commercially as SMARTPREP™ and as described in detail in Automated Detection of Bolus Arrival and Initiation of Data Acquisition in Fast, Three Dimensional, Gadolinium-Enhanced MR Angiography, by Foo T K L; Saranathan M; Prince M R; Chenevert T L, in *Radiology* 1997; 203:273–280, a monitor 306 is placed in close proximity to vessel 294 and upstream of the arterial blood flow for the field-of-view that constitutes scan station 286, an example of which is shown in FIG. 8. The precise positioning of monitor 306 is not critical, but preferably, it is positioned within the first 25% of the relevant scan station. The monitor 306 periodically detects MR signal excited in a small volume or region of vessel 294. The detected MR signal will reach a specified threshold level when the contrast agent enters that portion or segment of vessel 294 lying within scan station 286, at which time scanning of station 286 commences. When the scan is complete, the MR apparatus will sequentially proceed to acquire data from the subsequent scan stations 288 and 290.

As previously indicated, in prior art MRA techniques, the time required for the bolus 302 to travel from one scan station to the next has not been known, and since it varies from patient to patient, it would be advantageous to know such travel time. In the past, this could significantly diminish the benefits of using a contrast agent in conventional scan techniques or require the use of increased quantities or concentration of gadolinium chelate contrast material. Thus, in order to overcome such disadvantages in the prior art, and in accordance with one embodiment of the present invention, monitors 308 and 310 are directed toward vessel 294 in scan stations 288 and 290. Monitors 308 and 310 can then detect the arrival of bolus 302 within scan stations 288 and 290, respectively. The operation and construction of monitors 308 and 290 is similar to that of monitor 306.

According to this aspect of the present invention, there are two main algorithms to complete an MR image acquisition. The first, as shown in FIG. 9, is a test bolus travel time determination algorithm 312, and the second, is the MR image acquisition 314, as shown in FIG. 10, using the test bolus travel timing determination of FIG. 9.

Figure 9:
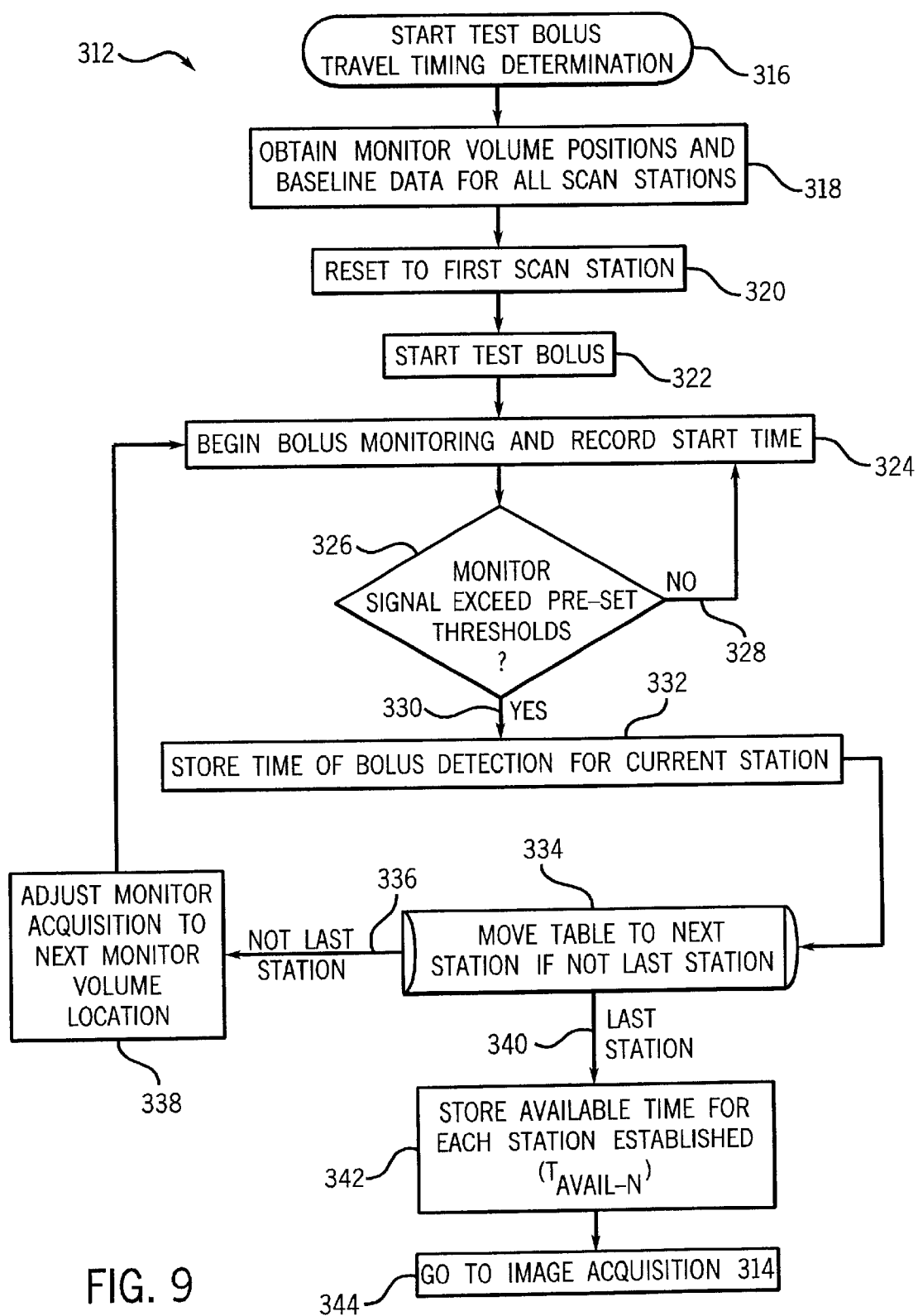
FIGS. 9 and 10 are flow charts illustrating an embodiment of the invention for use with the arrangement of FIG. 8.

Referring to FIG. 9, the first step in the test bolus travel timing determination algorithm 312 after startup 316 is to obtain monitor volume positions and baseline data for all scan stations 318. Baseline data is obtained from each monitor prior to acquisition of image data of the angiography exam in the absence of contrast agent. From such data, a threshold level may be reset for each monitor to indicate arrival of the bolus at the corresponding scan stations. These localized scans are typically referred to as scout views. The system is then reset to the first scan station and the test bolus is started 322 by injecting a small amount of contrast agent, typically 1–5 ml, injected at the same flow rate as a regular exam bolus. The test bolus begins to pass through the patient's peripheral vasculature as the algorithm records the start time and begins bolus monitoring 324. It is noted that the monitor volume 306, 308, and 310 can be located anywhere within the image field-of-view within each station, and preferably, can be placed exactly over the area of interest within the desired field-of-view. At which time the MR signal monitored is compared against a preset threshold 326, and if the monitored signal does not exceed the preset threshold 328, the start time is reset and bolus monitoring begins over again at 324. When the monitored signal exceeds the preset threshold 330, the time at which the bolus is detected for that scan station is stored 332. The patient table is moved to a next, or subsequent, scan station as long as the current scan station is not the last predefined scan station 334, 336. The monitor volume is then adjusted to acquire data at the next monitor volume location 338, at which time the system returns to begin bolus monitoring and recording the start time of that particular monitor volume at 324, and then continues to loop and acquire the travel time of the test bolus through each of the given number of scan stations until the last scan station is detected at 334, 340. The time available for acquiring imaging at a regular exam bolus, is then stored for each station as $T_{avail}$ at 342 and the system is then ready for regular MR image acquisition 344.

Figure 10:
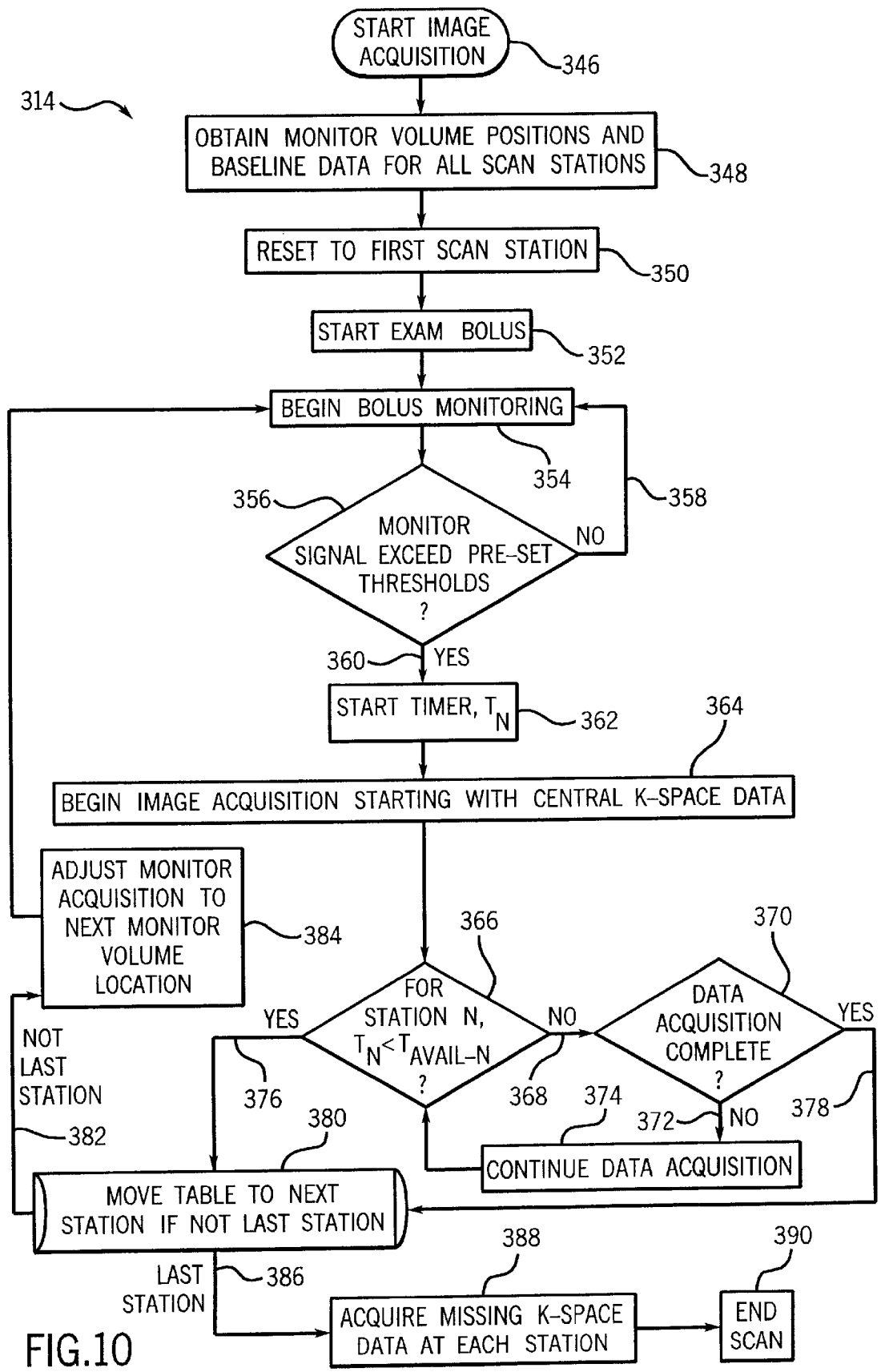

Referring to FIG. 10, the image acquisition algorithm 314 is shown, and after initialization 346, the monitor volume positions and baseline data for all scan stations are acquired 348. The system is then reset and the patient table is moved back to the first scan station 350 and the regular exam bolus is injected into the patient 352. Bolus monitoring is then commenced 354 while monitoring the monitor volume for the first scan station. The monitored signal is compared against the preset threshold 356, and if it does not exceed the preset threshold 358, the monitor rechecks for the presence of the bolus 354 until the monitored signal exceeds the preset threshold 360, at which time, the timer ($t_n$) is activated 362 and the MR apparatus begins image acquisition 364, starting primarily with the acquisition of central k-space data. The timer for that particular station is then compared to the test bolus travel time 366, and as long as the current data acquisition time is less than the test bolus travel time 368, and data acquisition is not yet complete 370, 372, the system continues to acquire data 374. Once either the data acquisition time for this particular scan station equals or exceeds the test bolus travel time 366, 376, or the system has acquired sufficient data 370, 378, the patient table is adjusted to the next scan station as long as the system is not currently at the last scan station 380, 382. After which, the system switches to acquire data at the next monitor volume location 384 and begins the bolus monitoring again at 354. The system then loops, as described, until data is acquired or the system times out for the last scan station 386. The system then returns to any scan station in which a full k-space data set had not been acquired, and acquires the. missing k-space data 388. Once all k-space data is acquired for all the scan stations, the image acquisition algorithm is concluded 390.

While FIG. 8 shows three scan stations 286, 288 and 290, it is readily apparent that in other embodiments, the number of scan stations n may be greater or less than that shown in the preferred embodiment. Moreover, as is readily apparent from FIG. 10, the initial data acquisition at each scan station is described as being limited to acquiring central k-space data, that is, the k-space data of low spatial frequencies. This acquisition can be expanded to acquire higher spatial frequency k-space data if time permits. However, it is recognized that the lower spatial frequency k-space data is the most significant in image reconstruction, and can be usefully acquired in approximately 5–10 seconds.

Figure 11:
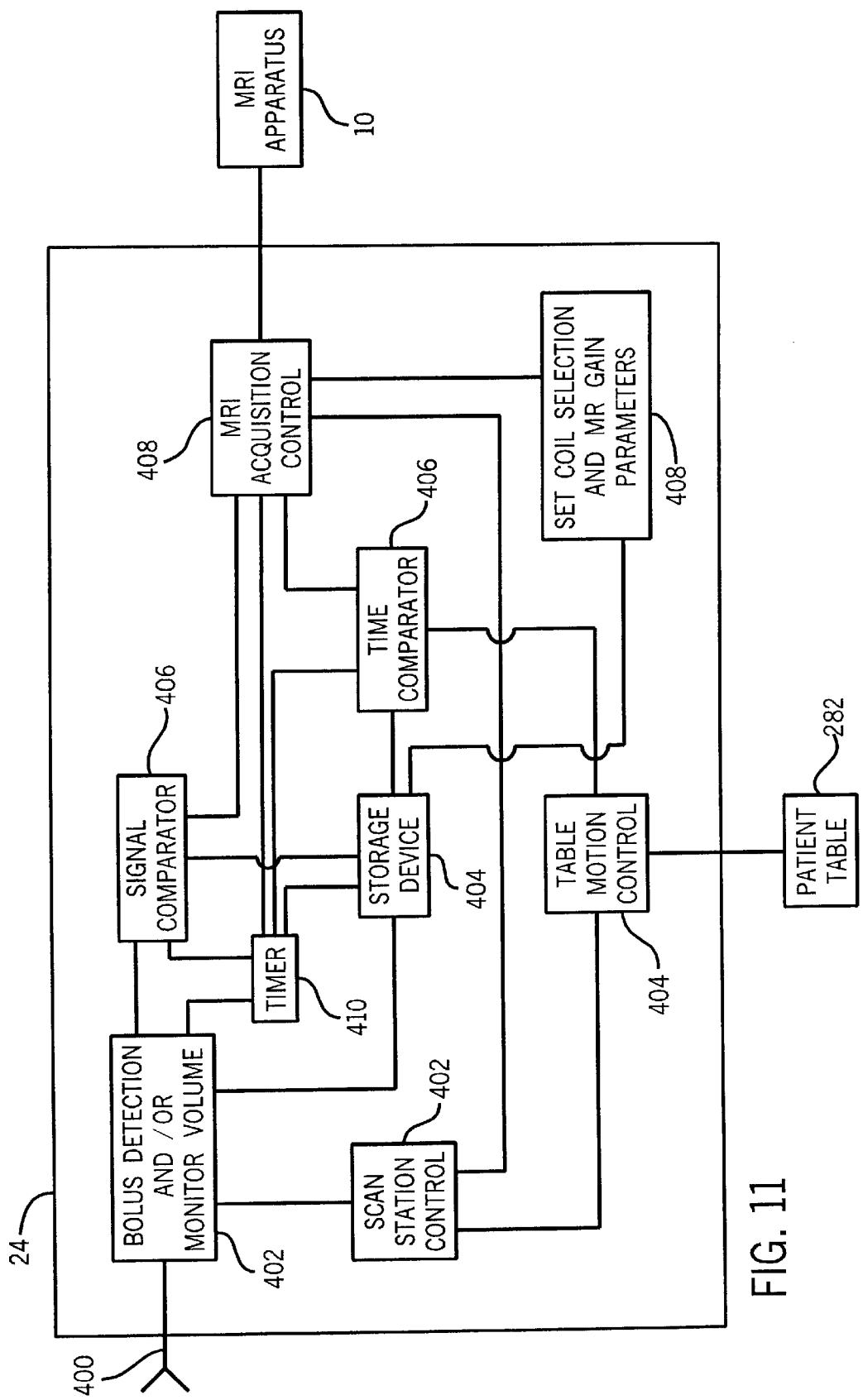
FIG. 11 is a block diagram of an embodiment of the invention incorporating the present invention as shown in FIGS. 1–10.

FIG. 11 shows a functional block diagram of computer 24 connected to MRI apparatus 10, as shown in FIG. 1, and to the movable patient table 282. The control has an input 400 that may be used for indicating the start of a test bolus and/or the exam bolus to the bolus detection 402. Additionally, or alternatively, bolus detection can be accomplished by the aforementioned monitor volume procedure, one example of which is the aforementioned commercially available SMARTPREP™ from the General Electric Company. The storage device 404 is connected to the bolus detection 402 and receives preset thresholds for comparing the monitored signal from the monitor volume. The preset thresholds are compared to the monitored signals in a signal comparator 406, the output of which is used in an MRI acquisition control 408, together with the output of a timer 410, to check the location of the bolus using MRI apparatus 10. The MRI acquisition control 408 also is connected to a scan station control 402 which controls patient table 282 through table motion control 404. The scan station control 402 is also connected to the bolus detection 402 in order to reset the patient table to the first scan station when a procedure is first initialized. Timer 410 is also connected to storage device 404 to store the maximum travel time that it takes the test bolus to travel through a given scan station. Timer 410 is also connected between a signal compared to 406 and the MRI acquisition control 408 and is used during image acquisition to time the current MRI acquisition and compare it in time comparator 406 with the maximum test bolus travel time as retrieved from the storage device 404. To optimize image acquisition, the stored values for the test bolus travel time, for each scan station, are used in the MRI acquisition control 408 to select the most desirable coil elements in MRI apparatus 10 and to set the optimal receiver and body coil transmitter gain parameters in MRI apparatus 10.

Accordingly, the present invention includes a method of identifying a stenotic vessel in a patient's peripheral arterial vasculature using MR imaging that includes performing a screening study by tracking passage of a contrast bolus through a patient while acquiring a series of first MR images having low resolution to locate any stenotic regions. The method then includes scanning the series of first MR images to identify a stenosis within the patient's peripheral arterial vasculature. The invention next includes performing a detailed study by acquiring a second MR image having a higher resolution than the series of first MR images for grading the identified stenosis.

Preferably, the series of first MR images are acquired to provide high sensitivity to lesion detection in a blood vessel. The steps of acquiring a second MR image and analyzing the second MR image are conditioned upon identifying a suspected stenosis in the previous step. If none is so identified, the exam can be completed without acquiring any further time consuming images. The series of first MR images are acquired with a pulse sequence having flow sensitizing bi-polar gradients. Also, a VENC value of a first moment of the flow sensitizing bi-polar gradients is initially set to a nominally low value to establish a velocity distribution greater than $2\pi$ within each voxel. When scanning or analyzing the series of first MR images, the detection of flow voids about a vessel is used as an indication of the presence of a stenosis. In order to acquire the series of first MR images with high phase cancellation, either a pulse sequence with bi-polar gradients to accentuate phase cancellation is used, or alternatively, the voxel size can be increased for greater distribution of velocity vectors, to thereby increase flow dephasing.

The invention also includes an examination method to identify a lesion in a blood vessel of a patient's peripheral arterial vasculature and grade a stenosis resulting therefrom. The examination method includes injecting a contrast agent in a patient and acquiring a series of first MR images using a gradient echo imaging pulse sequence having a flow sensitizing bi-polar gradient waveform as the bolus passes through the patient. The method next includes detecting and localizing a suspected stenosis in the series of first MR images. If a stenosis is identified and localized, the examination continues with acquiring a second MR image having a higher resolution than the first MR image in a region in which the suspected stenosis is detected and localized to then grade the suspected stenosis. Conversely, if a stenosis is not detected and localized, the examination is ended without further time consuming image acquisitions.

The second MR image can be acquired with low phase cancellation and high resolution in order to isolate and grade the suspected stenosis. This is accomplished by either comparing diameters of the blood vessel along a length of the suspected stenosis, or comparing a velocity gradient along the length of the suspected stenosis. Preferably, the second MR image is acquired to determine peak flow velocity across the stenosis by applying a real-time phase contrast imaging pulse sequence to the vessel to allow user control of the VENC value when acquiring the second MR image, and determining peak flow velocity across the stenosis by correlating the VENC value to an onset of flow velocity aliasing. The real-time phase contrast imaging pulse sequence has flow sensitizing gradients that are relatively coincident in time to allow a user to rotate flow sensitizing gradients in real-time. The amplitude of the VENC value can also be adjusted in real-time until flow related aliasing is detected. By acquiring a VENC value at the onset of flow related aliasing along the points of a stenosis, and comparing these VENC values, the severity of the stenosis can be accurately determined.

The aforementioned methods are incorporated into an MRI apparatus to conduct time-efficient MR stenosis screening of large vascular territories, and if necessary, grade individual stenotic vessel segments. The apparatus includes an MRI system having a plurality of gradient coils positioned about the bore of a magnet to impress a polarizing magnetic field, an RF transceiver system, and an RF switch controlled by a pulse module to transmit RF signals to an RF coil assembly to in turn acquire MR images. A computer is programmed to operate the MRI system in two modes to efficiently conduct the stenosis exam across the patient's peripheral arterial vasculature. The first mode is programmed to track passage of a contrast bolus through the patient's peripheral arterial vasculature while it acquires a series of first MR images with low resolution over the patient's peripheral arterial vasculature. The first mode also allows reception of an input to either end the stenosis exam or switch to the second mode if there is an indication of a stenosis in the first MR image. The second mode is programmed to localize a FOV to target the suspect stenosis, and then acquire at least one second MR image with resolution higher than that of the series of first MR images. The stenosis may be assessed using more than one second MR image.

The computer of the MRI apparatus is also programmed to use a first pulse sequence for the acquisition of the series of first MR images. The first pulse sequence has a flow sensitizing bi-polar gradient waveform. A second pulse sequence is then used for the acquisition of the second MR image. The second pulse sequence provides less phase cancellation than the first pulse sequence. The first pulse sequence also includes a VENC value of a first moment of the flow sensitizing bi-polar gradient waveform that is set to a nominally low value, that is substantially lower than that of the second pulse sequence.

Preferably, the series of first MR images results in an encoded velocity distribution that is greater than $2\pi$ within each voxel. The computer is programmed to increase flow dephasing in the series by either increasing in voxel size for greater distribution of the velocity vectors, or using a bi-polar gradient waveform as previously mentioned.

The invention also includes a computer readable storage medium having stored thereon a computer program having instructions which, when executed by a computer, cause the computer to acquire a series of first MR images of a patient's peripheral arterial vasculature. The series of first MR images have high phase cancellation to screen a patient for possible arterial lesions. Each of the first MR images in the series is acquired within a scan station, preferably, as the contrast bolus travels therethrough. The program also causes the computer to limit a FOV to a target region within the patient's peripheral arterial vasculature if an arterial lesion is located therein, and then acquires a second MR image of the targeted region. The second MR image has a resolution higher than that of the series of first MR images. The first MR images are acquired using either a pulse sequence with bi-polar gradients to accentuate phase cancellation, or an increased voxel size for greater distribution of velocity vectors, each to increase flow dephasing. The second MR image is acquired with low phase cancellation and high resolution in order to isolate and grade the suspected stenosis located with the series of first MR images. Such isolation and gradation is accomplished by either comparing diameters of the blood vessel along a length of the suspected stenosis, or comparing a velocity gradient along the length of the suspected stenosis.

The present invention has been described in terms of the preferred embodiment, and it is recognized that equivalents, alternatives, and modifications, aside from those expressly stated, are possible and within the scope of the appending claims.

The present invention has been described in terms of the preferred embodiment, and it is recognized that equivalents, alternatives, and modifications, aside from those expressly stated, are possible and within the scope of the appending claims.

We claim:

1. A method of identifying a stenotic vessel in a patient's peripheral arterial vasculature using MR imaging comprising the steps of:

performing a screening study by acquiring a series of first MR images having low spatial resolution along the patient's peripheral arterial vasculature as a contrast bolus passes therethrough;

scanning the series of first MR images to identify a stenosis in the patient's peripheral arterial vasculature; and performing a detailed study by acquiring at least one second MR image having higher resolution than the series of first MR images for grading the identified stenosis.

2. The method of claim 1 wherein each first MR image is acquired using a flow sensitive three-dimensional fast imaging pulse sequence.

3. The method of claim 2 wherein the flow sensitive three-dimensional fast imaging pulse sequence includes bi-polar gradients in three directions to provide insensitivity to orientation of the vessel and any stenosis.

4. The method of claim 3 further comprising the step of initially setting a velocity encoding (VENC) value of a first moment of the flow-sensitizing bi-polar gradient to a nominally low value to establish a velocity distribution geater than $2\pi$ within each voxel.

5. The method of claim 1 further comprising the step of applying a pulse sequence with flow-sensitizing bi-polar gradient in one direction when imaging a distal peripheral vasculature where flow is predominantly in a cranial-caudal direction.

6. The method of claim 1 wherein the series of first MR images provides high sensitivity to lesion detection in a blood vessel and wherein the step of scanning the series of first MR images includes detecting flow voids as an indication of a suspected stenosis.

7. The method of claim 1 further comprising the step of conditioning the acquisition of a second MR image upon identification of a stenosis in the step of screening the series of first MR images.

8. The method of claim 1 wherein the series of first MR images are acquired with high phase cancellation using at least one of:

(1) applying a pulse sequence with bi-polar gradients to accentuate phase cancellation; and (2) increasing voxel size for greater distribution of velocity vectors; to thereby increase flow dephasing.

9. The method of claim 1 wherein the second MR image is acquired with low phase cancellation and high resolution in order to isolate and grade the stenosis by at least one of:

(1) comparing diameters of the blood vessel along a length of the suspected stenosis;

(2) comparing a velocity gradient along the length of the stenosis; and (3) measuring blood flow along the suspected stenosis.

10. The method of claim 1 further comprising the step of tracking passage of a contrast bolus that includes:

passing a test bolus through the patient's peripheral vasculature;

tracking the test bolus through the patient's peripheral vasculature;

determining a travel time that the test bolus takes to travel through a desired portion of the patient's peripheral vasculature;

passing an exam bolus through the patient's peripheral vasculature at a flow rate; and using the test bolus travel time to track the passage of the exam bolus through the patient's peripheral vasculature.

11. The method of claim 10 further comprising the steps of:

defining a given number of scan stations, each scan station positioned along a patient's peripheral vasculature;

initially injecting a relatively small amount of contrast agent into a patient to pass the test bolus through the patient's peripheral vasculature; and adjusting the patient fore and aft with respect to an MR imaging device to position the patient such that a desired scan station is within a field-of-view of the MR imaging device based on the passage of the test bolus.

12. The method of claim 1 wherein the step of grading the stenosis includes determining peak flow velocity across the stenosis by:

applying a real-time phase contrast imaging pulse sequence to the vessel to allow user control of a flow encoding gradient value when acquiring the second MR image; and determining peak flow velocity across the stenosis by correlating the flow encoding gradient value to an onset of flow velocity aliasing.

13. The method of claim 12 wherein the real-time phase contrast imaging pulse sequence has flow sensitizing gradients that are relatively coincident in time to allow a user to rotate flow sensitizing gradients in real-time.

14. The method of claim 12 further comprising the step of increasing an amplitude of the flow encoding gradient value until flow-related aliasing is detected.

15. The method of claim 12 further comprising the step of applying flow sensitizing gradient in three directions to provide insensitivity to vessel orientation.

16. The method of claim 1 wherein the step of grading the stenosis comprises:

identifying a first location of a suspected stenosis;

applying a phase contrast MR imaging pulse sequence to the first location of the suspected stenosis, the pulse sequence having a real-time user-controlled VENC value;

increasing the real-time user-controlled VENC value and reapplying the pulse sequence until a user observes flow-related aliasing;

recording the real-time user-controlled VENC value as an indication of peak flow velocity across the first location of the suspected stenosis;

resetting the real-time user-controlled VENC value;

applying the pulse sequence to a second location of the suspected stenosis;

increasing the real-time user-controlled VENC value and reapplying the pulse sequence until the user observes flow-related aliasing;

recording the real-time user-controlled VENC value as an indication of peak flow velocity across the second location of the suspected stenosis; and comparing the real-time user-controlled VENC value of the first location with that of the second location to determine severity of the suspected stenosis.

17. The method of claim 15 wherein the phase contrast MR imaging pulse sequence is a 2D fast gradient echo pulse sequence having flow sensitizing bi-polar gradient waveforms that are relatively coincident in time.

18. The method of claim 15 wherein the step of increasing the real-time user-controlled VENC value is further defined as increasing an amplitude of a velocity encoding gradient until the VENC value corresponds to a peak flow velocity to thereby identify severity of the suspected stenosis.

19. An examination method to identify a lesion in a patient's peripheral arterial vasculature and grade a stenosis resulting therefrom comprising the step of:

injecting a contrast agent in a patient;

acquiring a series of first MR images using a gradient echo imaging pulse sequence having a flow sensitizing bi-polar gradient waveform across a patient's peripheral arterial vasculature;

detecting and localizing a suspected stenosis using the series of first MR images;

if a stenosis is detected and localized, acquiring at least one second MR image having a higher resolution than the series of first MR images in a region in which the suspected stenosis is detected and localized to grade the suspected stenosis; and if a stenosis is not detected and localized in the step detecting and localizing, ending the examination method without further MR image acquisition.

20. The method of claim 18 further comprising the steps of:

passing a contrast bolus through the patient's peripheral arterial vasculature and acquiring MR images coincident with the passage of the contrast bolus through the patient's peripheral arterial vasculature.

21. The method of claim 19 further comprising the steps of defining multiple stations to acquire the series of first MR images therein, and precisely moving to a next station using one of:

(1) contrast agent arrival monitoring, and (2) pre-calculating bolus travel times.

22. The method of claim 18 further comprising the step of assessing severity of the steno sis by measuring a VENC value in real-time coincident with an onset of complete intra-voxel flow dephasing.

23. The method of claim 18 further comprising the step of assessing severity of the stenosis by measuring a VENC value in real-time coincident with an onset of flow related aliasing in a stenotic vessel.

24. The method of claim 18 wherein the series of first MR images are low resolution images with high sensitivity to velocity flow for detecting blood vessel lesions.

25. The method of claim 23 wherein the step of detecting a blood vessel lesion includes detecting velocity flow voids in the series of first MR images.

26. The method of claim 18 wherein the series of first MR images are acquired with high phase cancellation to increase flow dephasing using at least one of:

(1) applying a pulse sequence with bi-polar gradients to accentuate phase cancellation; and (2) increasing voxel size for greater distribution of velocity vectors.

27. The method of claim 18 wherein the second MR image is acquired to grade the suspected stenosis by at least one of:

(1) comparing diameters of the blood vessel along a length of the suspected stenosis; and (2) comparing a velocity gradient along the length of the suspected stenosis.

28. An MRI apparatus to conduct MR stenosis screening, and if necessary, grade a stenotic vessel comprising:

a magnetic resonance imaging (MRI) system having a plurality of gradient coils positioned about a bore of a magnet to impress a polarizing magnetic field and an RF transceiver system and an RF switch controlled by a pulse module to transmit RF signals to an RF coil assembly to acquire MR images; and a computer programmed to operate the MRI system in two modes to efficiently conduct a stenosis exam across a patient's peripheral arterial vasculature, the first mode programmed to:
track passage of a contrast bolus through the patient's peripheral arterial vasculature;
acquire a series of first MR images with low resolution over the patient's peripheral arterial vasculature;
receive input to either end the stenosis exam or switch to a second mode if a stenosis is indicated in the series of first MR images;

the second mode programmed to:
localize a field-of-view to target the stenosis; and
acquire at least one second MR image with resolution higher than that of the series of first MR images of the localized field-of-view to assess a severity of the stenosis.

29. The MRI apparatus of claim 28 wherein the computer is further programmed to:
use a first pulse sequence for the acquisition of the series of first MR images, the first pulse sequence having a flow-sensitizing bi-polar gradient waveform and a VENC value of a first moment of the flow sensitizing bi-polar gradient waveform set to a nominally low value; and
use a second pulse sequence for the acquisition of the at least one second MR image, the second pulse sequence providing less phase cancellation than the first pulse sequence and having a VENC value set substantially higher than the VENC value of the first pulse sequence.

30. The MRI apparatus of claim 28 wherein an encoded velocity distribution is greater than $2\pi$ within each voxel in the series of first MR images.

31. The MRI apparatus of claim 28 wherein the acquisition of the at least one second MR image includes:
(a) applying a real-time phase contrast pulse sequence to a suspected stenotic vessel, where the pulse sequence has flow sensitizing gradients that are relatively coincident in time;
(b) allowing a user to adjust a VENC value of a velocity encoding gradient;
(c) applying the pulse sequence with the VENC value as adjusted by the user;
(d) determining whether flow-related aliasing is evident; and
(e) repeating acts (b) through (d) until the VENC value provides determinable flow-related aliasing that thus corresponds to a peak flow velocity across the suspected stenosis.

32. The apparatus of claim 31 wherein the computer is further programmed to increase an amplitude of the VENC value until flow-related aliasing is observable.

33. The MRI apparatus of claim 28 wherein the computer is further programmed to:
pass a test bolus through the patient's peripheral vasculature;
track the test bolus through the patient's peripheral vasculature;
determine a travel time that the test bolus takes to travel through a desired portion of the patient's peripheral vasculature;
pass an exam bolus through the patient's peripheral vasculature at a flow rate; and
use the test bolus travel time to track the passage of the exam bolus through the patient's peripheral vasculature.

34. The MRI apparatus of claim 28 wherein the computer is further programmed to:
(a) ensure placement of a patient table within the MRI apparatus and within a first scan station of a given number of scan stations;
(b) upon an indication that a test bolus has entered a given scan station, track the test bolus through the given scan station;
(c) record a travel time of the test bolus through the first scan station;
(d) initiate patient table movement to a subsequent scan station;
(e) repeat (b), (c) and (d) for each subsequent scan station;
(f) return the patient table to the first scan station; and
(g) upon an indication that an exam bolus has been injected into the patient, activate the MRI apparatus to acquire at least central k-space MRI data of the patient within each scan station for each test bolus travel time as previously recorded for that scan station.

35. A computer readable storage medium having stored thereon a computer program comprising instructions which, when executed by a computer, cause the computer to:
acquire a series of first MR images of a patient's peripheral arterial vasculature, the first MR image having high phase cancellation to screen a patient for possible arterial lesions, each first MR image in the series of first MR images is acquired within a scan station as a contrast bolus travels therethrough; and
limit a FOV to a target region within the patient's peripheral arterial vasculature if a lesion is located therein, then
acquire a second MR image of the targeted region, the second MR image having a resolution higher than that of the first MR image.

36. The computer readable storage medium of claim 35 wherein the series of first MR images are acquired with high phase cancellation to increase flow dephasing using at least one of:
(1) applying a pulse sequence with bi-polar gradients to accentuate phase cancellation; and
(2) increasing voxel size for greater distribution of velocity vectors.

37. The computer readable storage medium of claim 35 wherein the computer is further programmed to:
use a first pulse sequence for the acquisition of the series of first MR images, the first pulse sequence having a flow-sensitizing bi-polar gradient waveform; and
use a second pulse sequence for the acquisition of the at least one second MR image, the second pulse sequence providing less phase cancellation than the first pulse sequence.

38. The computer readable storage medium of claim 35 wherein the computer is further programmed to:
  apply a pulse sequence with at least one flow-sensitizing bi-polar gradient;
  initially set a velocity encoding (VENC) value of a first moment of the at least one flow-sensitizing bi-polar gradient to a nominally low value to establish a velocity distribution greater than $2\pi$ within each voxel; and
  detect velocity flow voids in the series of first MR images as an indication of any lesions.

39. The computer readable storage medium of claim 35 wherein the computer is further programmed to acquire the second MR image with low phase cancellation and high resolution in order to isolate and grade the suspected stenosis by at least one of:
  (1) comparing diameters of the blood vessel along a length of the suspected stenosis; and
  (2) comparing a velocity gradient along the length of the suspected stenosis.

40. The computer readable storage medium of claim 35 wherein the computer is further programmed to acquire the second MR image by:
  applying a real-time phase contrast imaging pulse sequence to the vessel to allow user control of a flow encoding gradient value when acquiring the second MR image; and
  determining peak flow velocity across the stenosis by correlating the flow encoding gradient value to an onset of flow velocity aliasing.

41. The computer readable storage medium of claim 40 wherein the real-time phase contrast imaging pulse sequence has flow sensitizing gradients that are relatively coincident in time to allow a user to rotate flow sensitizing gradients in real-time.

42. The computer readable storage medium of claim 40 wherein the computer is further programmed to increase an amplitude of the flow encoding gradient value until flow related aliasing is detected.

43. The computer readable storage medium of claim 40 having stored thereon a computer program comprising instructions which, when executed by a computer, cause the computer to grade the stenosis by:
  identifying a first location of a suspected stenosis;
  applying a phase contrast MR imaging pulse sequence to the first location of the suspected stenosis, the pulse sequence having a real-time user-controlled VENC value;
  increasing the real-time user-controlled VENC value and reapplying the pulse sequence until a user observes flow-related aliasing;
  recording the real-time user-controlled VENC value as an indication of peak flow velocity across the first location of the suspected stenosis;
  resetting the real-time user-controlled VENC value;
  applying the pulse sequence to a second location of the suspected stenosis;
  increasing the real-time user-controlled VENC value and reapplying the pulse sequence until the user observes flow-related aliasing;
  recording the real-time user-controlled VENC value as an indication of peak flow velocity across the second location of the suspected stenosis; and
  comparing the real-time user-controlled VENC value of the first location with that of the second location to determine severity of the suspected stenosis.

44. The computer readable storage medium of claim 40 wherein the computer is further programmed to track the contrast bolus through the patient's peripheral arterial vasculature by:
  passing a test bolus through the patient's peripheral vasculature;
  tracking the test bolus through the patient's peripheral vasculature;
  determining a travel time that the test bolus takes to travel through a desired portion of the patient's peripheral vasculature;
  passing an exam bolus through the patient's peripheral vasculature at a flow rate; and
  using the test bolus travel time to track the passage of the exam bolus through the patient's peripheral vasculature.

* * * * *